(12) United States Patent
Balding

(10) Patent No.: US 6,641,602 B2
(45) Date of Patent: Nov. 4, 2003

(54) METHOD AND DEVICE INCLUDING A COLO-RECTAL HEAT EXCHANGER

(75) Inventor: David P. Balding, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 10/120,589

(22) Filed: Apr. 11, 2002

(65) Prior Publication Data
US 2002/0151943 A1 Oct. 17, 2002

Related U.S. Application Data
(60) Provisional application No. 60/283,331, filed on Apr. 13, 2001.

(51) Int. Cl.⁷ .................................................. A61F 7/00
(52) U.S. Cl. ........................ 607/105; 607/104; 604/113
(58) Field of Search .................. 607/96, 104, 105; 604/113

(56) References Cited

U.S. PATENT DOCUMENTS

| | | |
|---|---|---|
| 2,058,780 A | 1/1936 | Elliot |
| 2,077,453 A | 4/1937 | Albright |
| 3,125,096 A | 3/1964 | Antiles et al. |
| 3,238,944 A | 3/1966 | Hirschhorn |
| 3,369,549 A | 2/1968 | Armao |
| 3,425,419 A | 2/1969 | Dato |
| 3,460,538 A | 8/1969 | Armstrong |
| 4,111,209 A | 9/1978 | Wolvek et al. |
| 4,662,383 A | 5/1987 | Sogawa et al. |
| 4,676,258 A | 6/1987 | Inokuchi et al. |
| 4,860,744 A | 8/1989 | Johnson et al. |
| 4,941,475 A | 7/1990 | Williams et al. |
| 4,955,377 A * | 9/1990 | Lennox et al. ............ 607/105 |
| 5,100,388 A | 3/1992 | Behl et al. |
| 5,106,360 A | 4/1992 | Ishiwara et al. |
| 5,151,100 A | 9/1992 | Abele et al. |
| 5,188,602 A | 2/1993 | Nichols |
| 5,195,965 A * | 3/1993 | Shantha .................... 607/105 |
| 5,211,631 A | 5/1993 | Sheaff |
| 5,257,977 A * | 11/1993 | Eshel ........................ 604/113 |
| 5,279,598 A | 1/1994 | Sheaff |
| 5,304,214 A | 4/1994 | DeFord et al. |
| 5,486,208 A | 1/1996 | Ginsburg |
| 5,496,271 A | 3/1996 | Burton et al. |
| 5,509,929 A | 4/1996 | Hascoet et al. |
| 5,545,137 A | 8/1996 | Rudie et al. |
| 5,591,162 A | 1/1997 | Fletcher et al. |
| 5,624,392 A | 4/1997 | Saab |
| 5,800,486 A | 9/1998 | Thome et al. |
| 5,800,493 A | 9/1998 | Stevens et al. |
| 5,827,269 A | 10/1998 | Saadat |
| 5,902,268 A | 5/1999 | Saab |
| 5,957,917 A | 9/1999 | Doiron et al. |
| 5,957,963 A | 9/1999 | Dobak, III |
| 6,009,351 A | 12/1999 | Flachman |
| 6,042,559 A | 3/2000 | Dobak, III |
| 6,051,019 A | 4/2000 | Dobak, III |
| 6,096,068 A | 8/2000 | Dobak, III et al. |
| 6,122,551 A | 9/2000 | Rudie et al. |
| 6,224,624 B1 | 5/2001 | Lasheras et al. |
| 6,228,048 B1 * | 5/2001 | Robbins .................... 604/31 |
| 6,231,594 B1 * | 5/2001 | Dae ........................... 607/96 |
| 6,231,595 B1 | 5/2001 | Dobak, III |
| 6,235,048 B1 | 5/2001 | Dobak, III |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,312,452 B1 | 11/2001 | Dobak, III et al. |
| 6,383,210 B1 | 5/2002 | Magers et al. |
| 6,506,189 B1 * | 1/2003 | Rittman, III et al. ......... 606/41 |

* cited by examiner

Primary Examiner—Roy D. Gibson
(74) Attorney, Agent, or Firm—John L. Rogitz (57) ABSTRACT

A method of regulating the temperature of a patient by inserting a heat exchange catheter into a colon of a patient. The heat exchange catheter is inflated with a heat exchange fluid from a temperature control unit wherein the heat exchange fluid is not infused into the patient. The heat exchange catheter has a catheter body with an inflow lumen, an outflow lumen, and an irrigation lumen for irrigating the colon.

11 Claims, 8 Drawing Sheets

METHOD AND DEVICE INCLUDING A COLO-RECTAL HEAT EXCHANGER

This application claims the benefit of Provisional Application No. 60/283,331 filed Apr. 13, 2001.

FIELD OF THE INVENTION

The present invention generally relates to a method and apparatus for regulating patient temperature, and more particularly, to a heat exchange catheter for insertion into the colon.

BACKGROUND OF THE INVENTION

There are a variety of medical conditions where it is desirable to regulate body temperature by either warming, cooling or maintaining the temperature of a patient. Examples of medical conditions where temperature regulation is warranted include accidental hypothermia, fever, therapeutic hypothermia, and warming or maintenance of normothermia during surgery or recovery.

Therapeutic hypothermia has proven useful in the treatment of stroke, SAH (subarachnoid hemorrhage), head injury and in other ailments. During surgery, a hypothermic state may reduce swelling, blood loss, and other adverse bodily reactions to surgery. It is expected that other therapeutic benefits of regulating the body temperature will manifest according to further development in this field.

U.S. Pat. No. 6,146,411 describes a system that relies on an indwelling heat exchange catheter for regulating a patient's temperature. The catheter inserts into the central vascular of a patient, heats or cools the blood supply, and thereby regulates the patient temperature.

U.S. Pat. No. 6,126,684 describes several types of vascular heat exchange catheters. One catheter includes a fluid that is heated or cooled from an external source and circulates through the catheter to exchange heat. A balloon is disclosed as one way of providing a heat exchange element, through which, the fluid circulates. One benefit of the balloon design is that the balloon can collapse for insertion and expansion in situ. Circulating a heat exchange fluid through an expandable balloon provides increase surface area, and thus improved heat exchange capacity.

One drawback of vascular heat exchange catheters is that the amount of heat exchange possible is limited by the maximum temperature that the heat exchange fluid can be heated. Studies show that blood thickens when heated beyond 41° C. Accordingly, vascular heat exchangers typically do not heat the blood beyond this temperature and, therefore, are limited in the ability to deliver heat transfer.

What is desired is an improved method and apparatus for heating a patient that can be used separate from, or in conjunction with, a vascular heat exchange catheter.

SUMMARY OF THE PRESENT INVENTION

The present invention provides a method and apparatus for regulating the temperature of a patient through insertion of a heat exchange catheter into the colon.

In accordance with one aspect of the present invention, a method of regulating the temperature of a patient includes the steps of inserting a heat exchange catheter into a colon of a patient. The heat exchange catheter has a proximal end, a distal end, an inflow lumen, an outflow lumen, and an irrigation lumen.

The heat exchange catheter is inflated with at least one heat exchange fluid from a temperature control unit through the inflow lumen wherein the heat exchange fluid is circulated through the catheter.

In accordance with another aspect of the invention, the method of regulating the temperature of a patient includes the steps of irrigating the colon with an irrigation solution through the irrigation lumen of the heat exchange catheter, inflating the heat exchange catheter at least once, and then deflating the heat exchange catheter at least once to regulate efflux of irrigation solution.

The method of regulating the temperature of a patient includes regulating pressure inside the catheter body. The step of regulating pressure inside the catheter body includes actuating a valve on the outflow lumen.

In accordance with a further aspect of the invention, the method includes inserting the heat exchange catheter into the colon, irrigating the colon, inflating the heat exchange catheter, deflating the heat exchange catheter, and flushing the colon by removing the irrigation fluid from the colon.

In accordance with a further aspect of the present invention, a heat exchange catheter for inserting into the colon includes a catheter body having a proximal end, a distal end, an inflow lumen, an outflow lumen, and an irrigation lumen. A self-contained fluid circuit is in fluid communication with the inflow lumen and outflow lumen for effecting heat exchange with the catheter body. A heat exchange fluid is circulated through the catheter body.

The catheter body has an exterior surface that expands. In addition, the catheter body has at least one flex zone to permit conformance to the intestinal anatomy of the patient.

The present invention provides several advantages including avoiding the associate risk of infections and thrombosis involved with intra vascular devices where a solution is inserted into the blood stream resulting in change in a patient's fluid balance. In addition, the body core can be heated and/or cooled at a rapid rate due to the large surface area within the colon.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION

There are a variety of medical conditions where it is desirable to regulate the body temperature of a patient by heating or cooling the patient. The present invention provides a method of regulating the temperature of a patient by inserting a heat exchange catheter into the colon.

Figure 1:
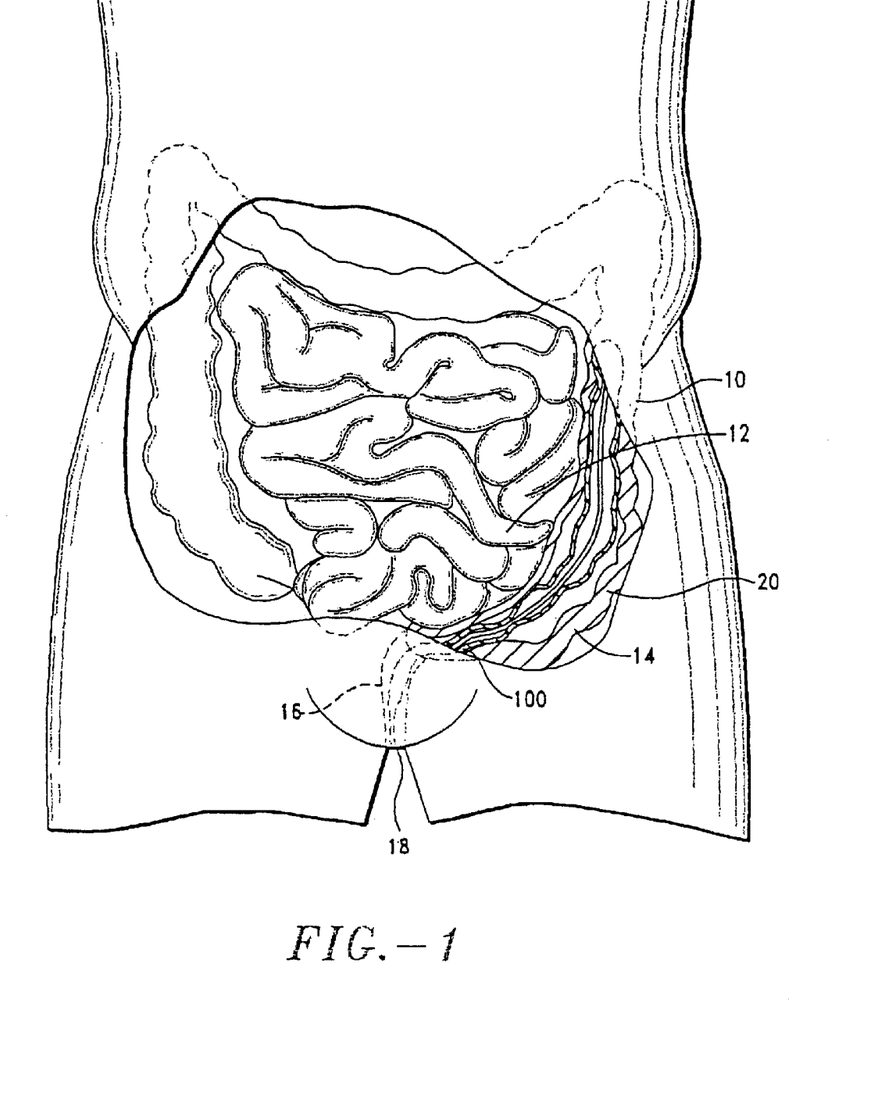
FIG. 1 is a cross-sectional view of a patient's digestive tract.

As shown in FIG. 1, the digestive tract 10 is a series of hollow organs. The digestive tract 10 comprises the mouth, esophagus, stomach, small intestine 12, large intestine 14, rectum 16, and anus 18. The last five to six feet of the large intestine 14 is known as the colon 20. The colon 20 is a muscular tube approximately 5 to 5½ feet in length with an average diameter of approximately 2½ inches. A heat exchange catheter 100 inserts into the colon 20 via the anus 16.

Figure 2:
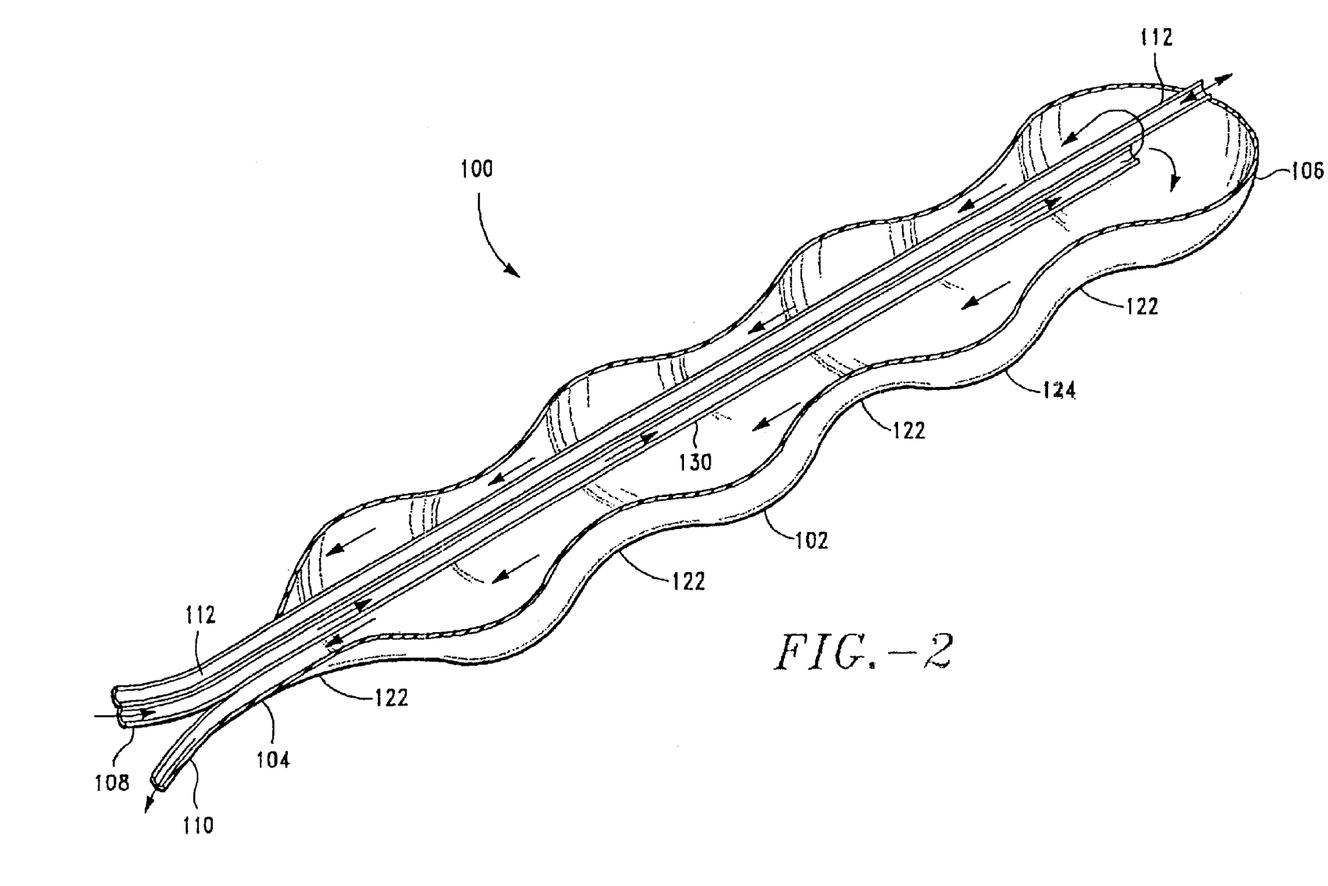
FIG. 2 is a cross-sectional view of a heat exchange catheter in accordance with the present invention.

FIG. 2 shows a heat exchange catheter 100. The catheter 100 includes a catheter body 102 having a proximal end 104, a distal end 106, an inflow lumen 108, an outflow lumen 110, and an irrigation lumen 112 for irrigation of the digestive tract.

The catheter body 102 is generally comprised of a system of tubes and/or balloons wrapped around an inlet lumen 130 for circulating a heat exchange fluid through the catheter body. The catheter body 102 has an exterior surface area 124 which expands upon the insertion of the heat exchange fluid. As a result of the expansive characteristics of the catheter body 102, the patient can be heated and/or cooled at a rapid rate due to the large surface area within the colon. It can be appreciated, however, that the catheter body can be comprised of any type of circulating material or design, including membranes and fibers for circulating the heat exchange fluid.

The exterior surface 124 of the catheter body 102 has at least one flex zone 122. The flex zone 122 provides flexibility to the exterior surface of the catheter body, and allows conformance of the catheter body 102 to the intestinal anatomy of the patient. Furthermore, the catheter body 102 with its system of tubes and/or balloons and flex zones 122 allows selective inflation and deflation of the catheter body for regulating heat exchange within the digestive tract.

A self-contained heat exchange fluid circuit connects a temperature control unit to the inflow lumen 108, and the outflow lumen 110 of the catheter body 102. The temperature control unit pumps a heat exchange fluid into the catheter body 102 via the inflow lumen 108 at the proximal end 104 of the heat exchange catheter 100. The heat exchange fluid traverses the catheter body 102 through the inlet lumen 130 to the distal end 106. From the distal end 106, the heat exchange fluid returns via the catheter body 102 to the outflow lumen 110. The heat exchange fluid exits the catheter body 102 at the proximal end 104 through the outflow lumen 110. The heat exchange fluid returns to the temperature control unit, wherein the heat exchange fluid is treated and returned to the catheter body 102.

The catheter body 102 also has an irrigation lumen 112 which extends from the proximal end 104 to the distal end 106 of the catheter body. An irrigation unit pumps an irrigation solution to the proximal end 104 of the catheter body 102 into the irrigation lumen 112. The irrigation solution traverses the catheter body 102 to the distal end 106 of the catheter body. At the distal end 106 of the catheter body 102, the irrigation fluid exits into the digestive tract. The irrigation solution cleanses the digestive tract in preparation for inflation of the catheter body 102. The cleaning of the digestive tract 10 results in improved heat exchange between the heat exchange catheter 100 and colon 20. The irrigation solution may also contain medications or other beneficial agents for delivery to the digestive tract.

The temperature, pressure, and flow rate of the heat exchange fluid is regulated externally. It can be appreciated, however, that the heat exchange catheter 100 can be equipped with sensors and supplemental heating/cooling elements to further monitor and regulate the temperature, pressure and flow rate of the heat exchange fluid. Optimally, the heat exchange catheter is designed for insertion into the digestive tract, however, it is conceivable that the catheter could be used in various other organs of the body.

Figure 3:
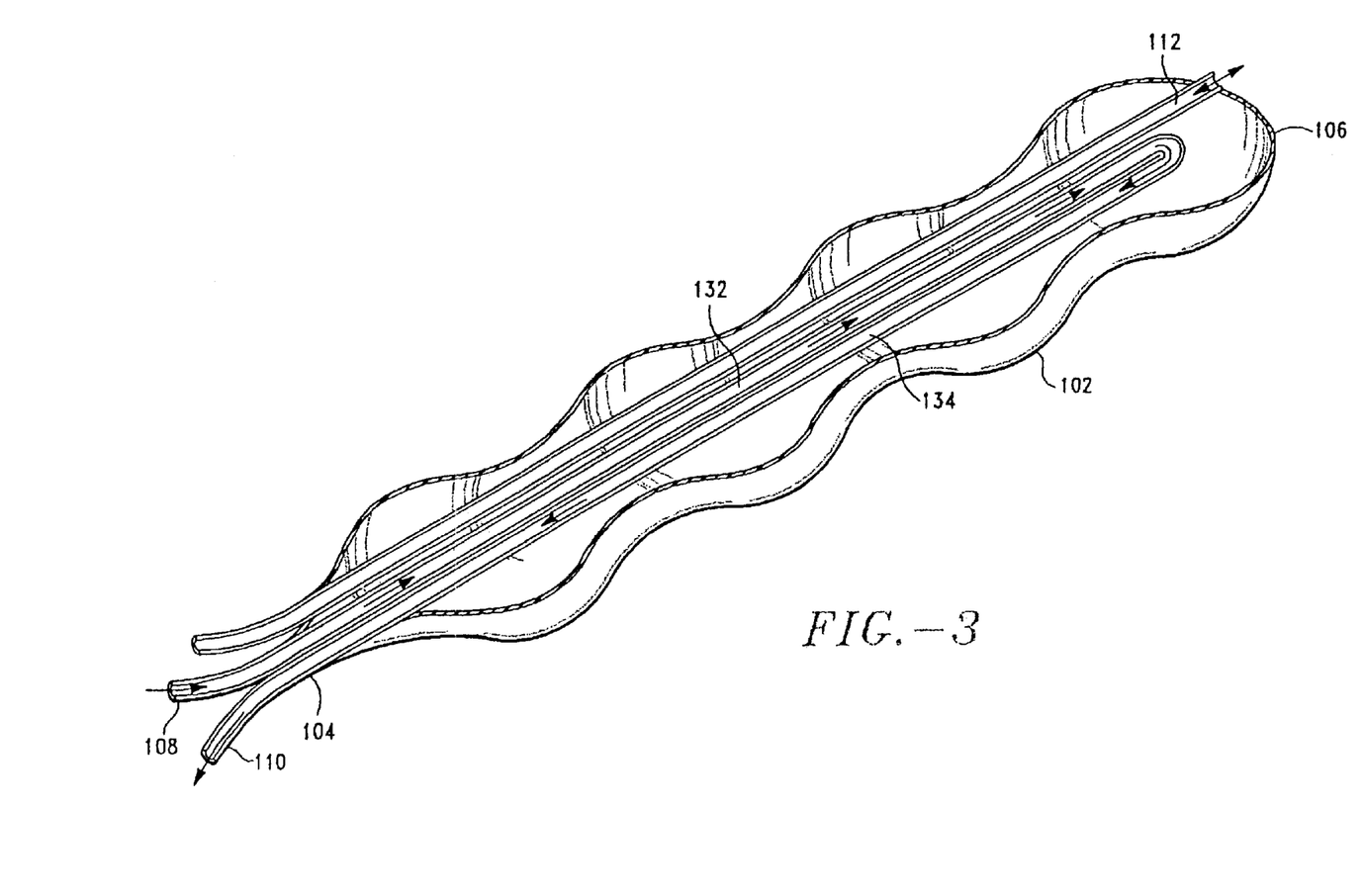
FIG. 3 is a cross-sectional view of another embodiment of the heat exchange catheter in accordance with the present invention.

FIG. 3 shows the catheter body 102 with a separate inlet lumen 132 and separate outlet lumen 134. The inlet lumen 132 extends from the proximal end 104 of the catheter body 102 to the distal end 106 of the catheter body 102. At the distal end 106 of the catheter body 102, the inlet lumen 132 makes a 180 degrees turn, to form an outlet lumen 134. The temperature control unit pumps the heat exchange fluid into the catheter body 102 through the inflow lumen 108. The heat exchange fluid traverses the inlet lumen 132 until the fluid reaches the distal end 106. The heat exchange fluid then returns via the outlet lumen 134 to the proximal end 104 of the catheter body 102.

Figure 4:
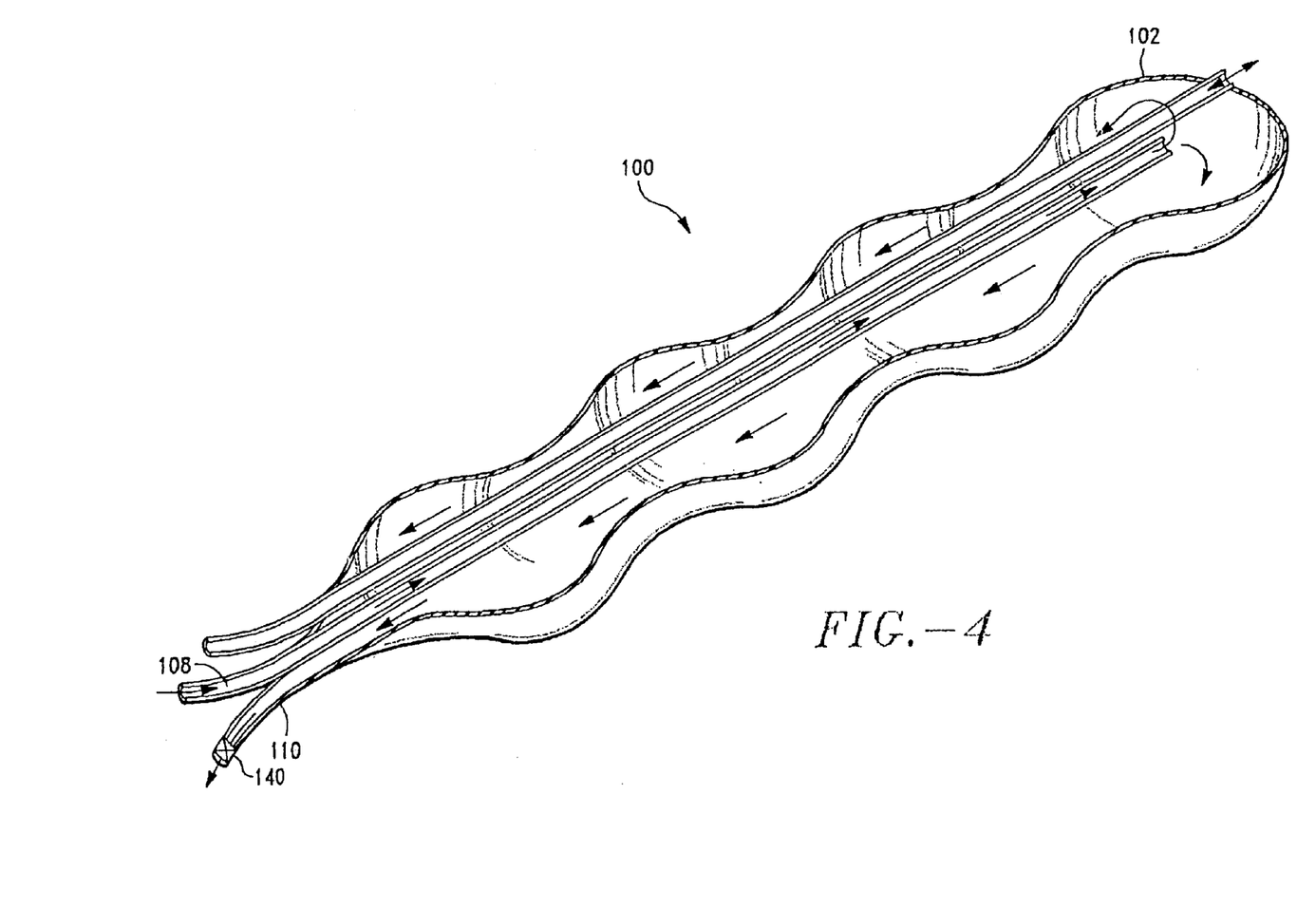
FIG. 4 is a cross-section view of another embodiment of the heat exchange catheter in accordance with the present invention.

FIG. 4 shows another embodiment of the heat exchange catheter 100. In this embodiment an actuating valve 140 attaches to the outflow lumen 110. The actuating valve 140 regulates the pressure of the heat exchange fluid within the catheter body 102. The catheter body 102 expands upon increasing the pressure within the catheter body 102, and decreases in size upon reducing the pressure within the catheter body. In addition, the actuating value regulates the size and shape of the catheter body 102 to promote conformance of the catheter body 102 to the anatomy of the patient's intestine.

Figure 5:
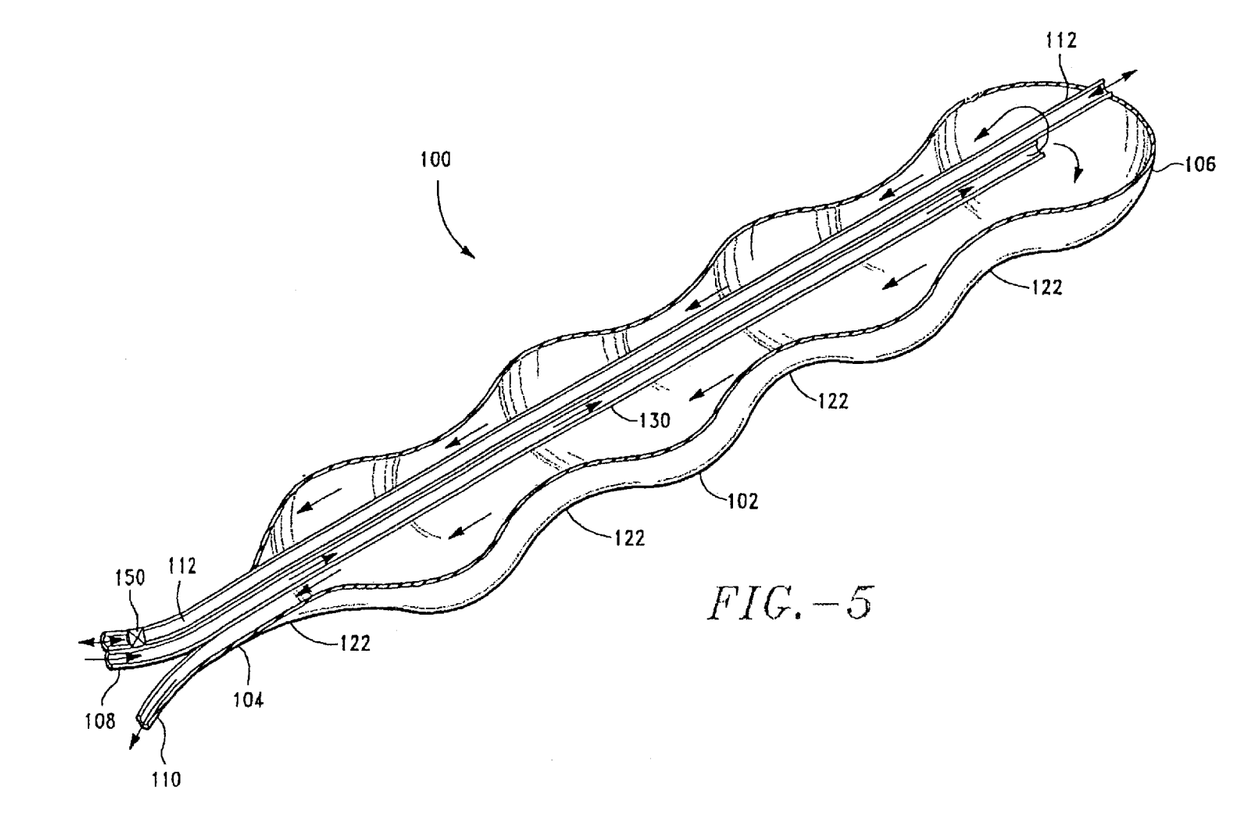
FIG. 5 is a cross-section view of another embodiment of the heat exchange catheter in accordance with the present invention.

In another embodiment, as shown in FIG. 5, the irrigation lumen 112 has a valve 150 to regulate the flow of the irrigation solution. The irrigation lumen 112 extends from the proximal end 104 of the catheter body 102 to the distal end of the catheter body 112. The valve 150 can be located on the proximal end 104 as shown in FIG. 5 or at the distal end 106 (not shown). It can be appreciated that the valve 150 may be a one way valve, a two-way valve or any other type of valve depending on the specific design and use of the catheter.

Figure 6:
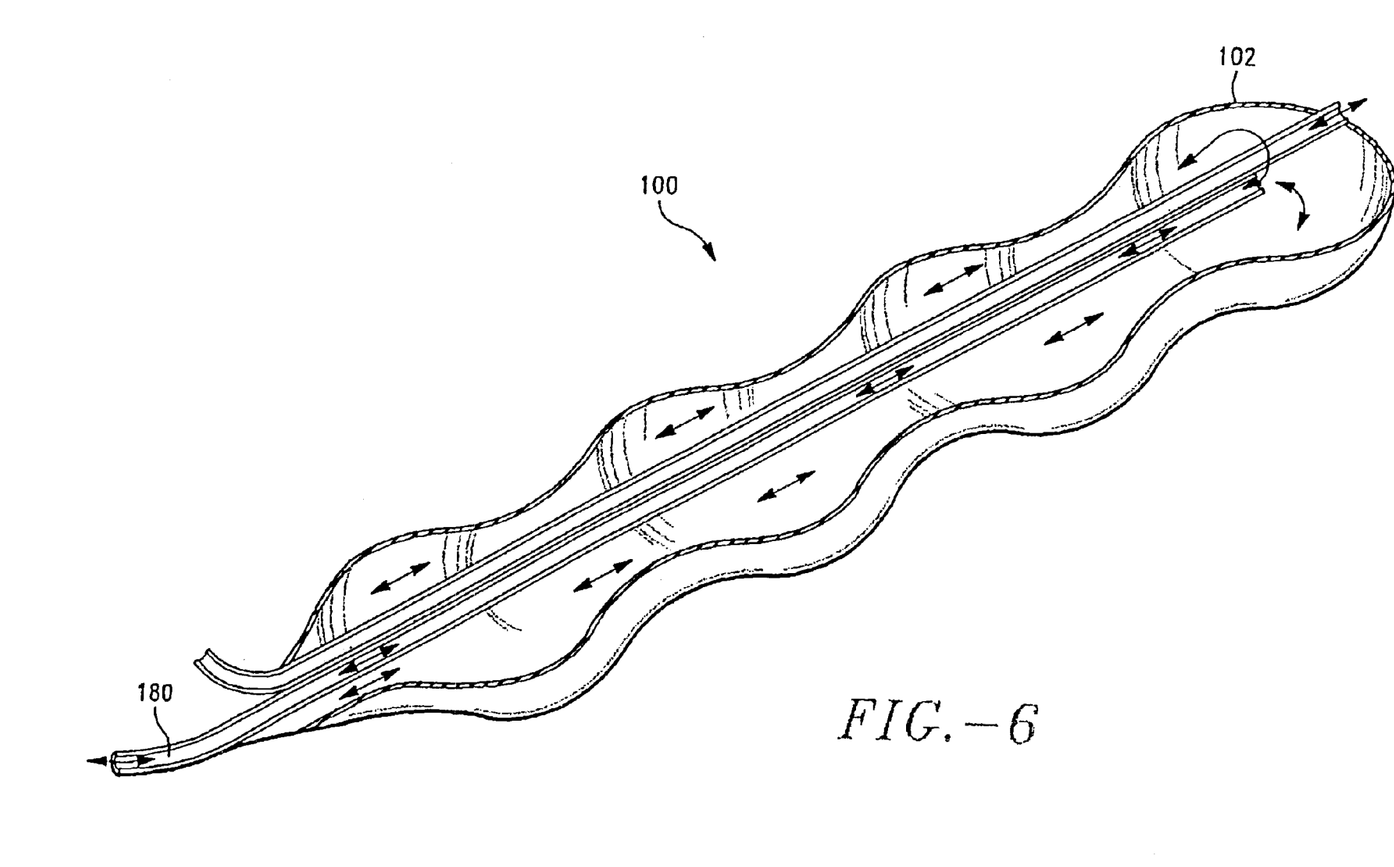
FIG. 6 is a cross-section view of another embodiment of the heat exchange catheter in accordance with the present invention.

FIG. 6 shows the catheter body 102 with a single heat exchange fluid lumen 180 which extends from the proximal end 104 to the distal end 106 of the catheter body 102. The temperature control unit pumps the heat exchange fluid into the catheter body 102 through the lumen 180. The heat exchange fluid traverses the length of the catheter body 102 and exits at the distal end 106. The heat exchange fluid fills the catheter body 102 causing the catheter body to expand to conform to the patient intestinal anatomy. The heat exchange fluid is then removed though the lumen 180 to the temperature control unit. The insertion and removal of the heat exchange fluid are repeated resulting in an unidirectional flow of heat exchange fluid.

In Operation

This invention relates to various methods of regulating the temperature of a patient using a heat exchange catheter 100 in the digestive tract. These techniques may be implemented using the representative catheter 100 described above, or with alternate catheters designed for use in the digestive tract. For medical purposes, the digestive tract generally is irrigated before insertion of the heat exchange catheter into the digestive tract. Irrigation of the digestive tract can include medications, enemas, or any acceptable method for irrigating or stimulating evacuation of the digestive tract. The methods of use of the catheter will be explained in further detail below.

Figure 7:
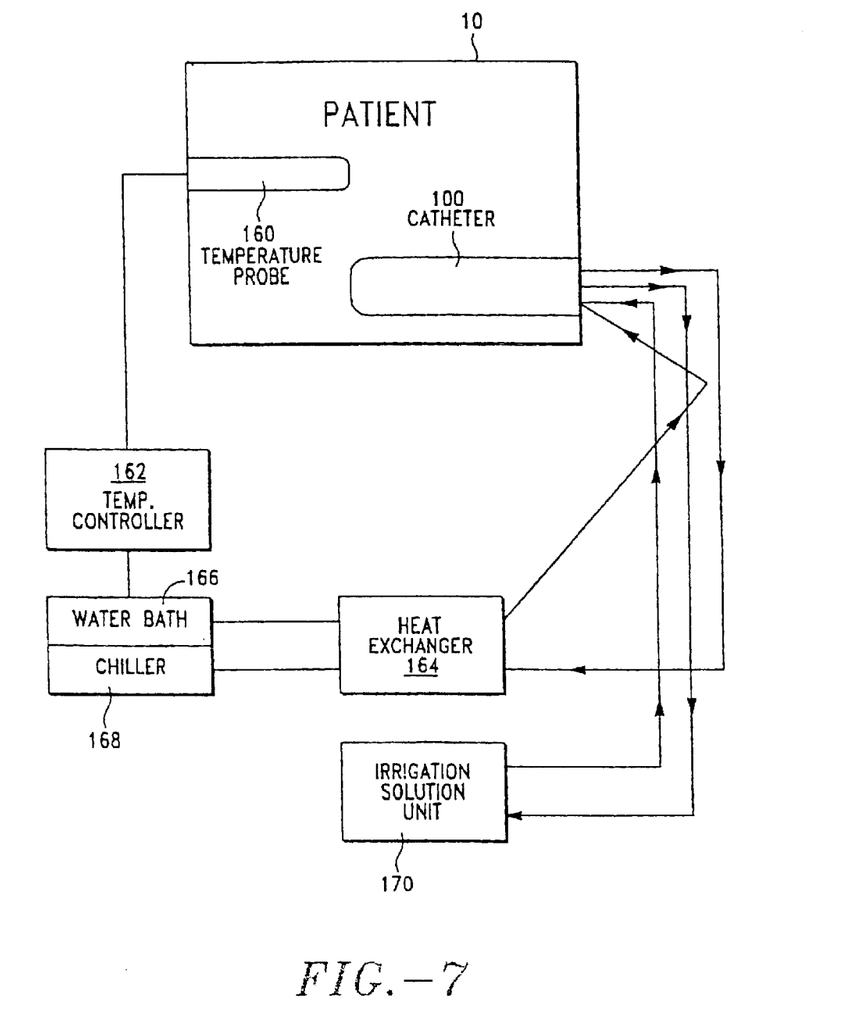
FIG. 7 is a flow diagram illustrating the general operation of the heat exchange catheter in accordance with the present invention.

As shown in FIG. 7, a system for exchanging heat with the body of a patient for cooling or heating the patient 10 is generally comprised of a heat exchange catheter 100, a temperature probe 160, a temperature control unit 162, a heat exchanger 164, a water bath 166, a chiller 168, and an irrigation solution unit 170.

Figure 8:
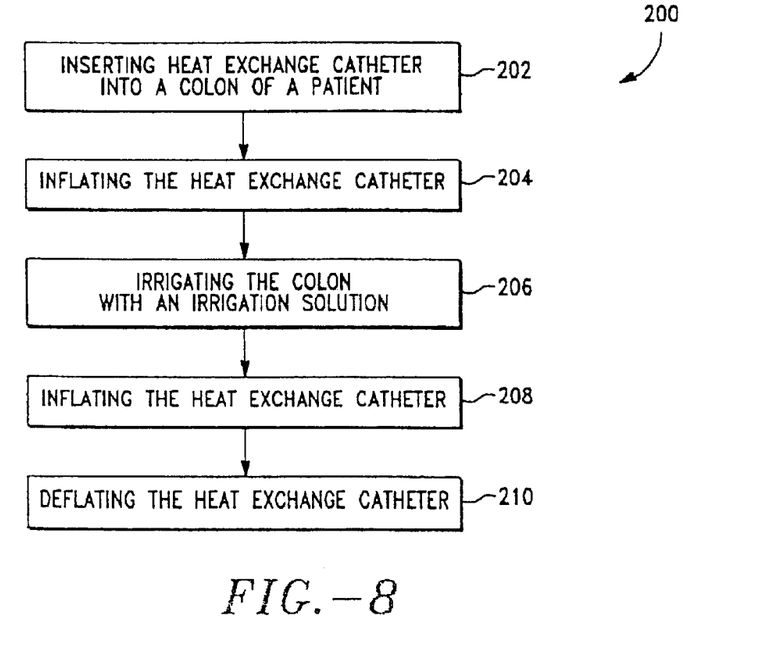
FIG. 8 is a flow diagram illustrating the method of regulating the temperature of a patient.

In FIG. 8, a method of regulating the temperature of a patient is shown. The method 200 includes the steps of inserting a heat exchange catheter into the digestive tract of a patient 202. The heat exchange catheter is then inflated with at least one heat exchange fluid which is circulated through the catheter body 204.

The heat exchange catheter body has a proximal end, a distal end, an inflow lumen, an outflow lumen, and an irrigation lumen. The temperature control unit pumps the heat exchange fluid to the catheter which circulates the heat exchange fluid through the inflow lumen, and outflow lumen.

The digestive tract is then irrigated with an irrigation solution through the irrigation lumen of the heat exchange catheter 206. The irrigation of the digestive tract cleanses the digestive tract to avoid complications, if the digestive tract is not cleaned with an irrigation solution. In addition, cleansing the digestive tract improves heat exchange between the catheter body and the walls of the digestive tract.

The heat exchange catheter is then inflated with at a heat exchange fluid from the temperature control unit 208. The heat exchange catheter is then deflated 210, and the irrigation solution removed or flushed from the digestive tract. The inflation and deflation of the heat exchange catheter occur at least once to regulate the efflux of irrigation solution into the digestive tract.

In another embodiment, the pressure inside the catheter body is regulated. An actuating valve within the outflow lumen regulates the pressure of the heat exchange fluid on the inside of the exterior surface of the catheter body. The regulation of the pressure within the catheter body allows the exterior surface area of the catheter body to expand, and permit conformance to the intestinal anatomy of the patient. In addition, the expansion of the catheter body allows the catheter body to have greater surface area contact within the digestive tract which maximizes the heating and cooling capacity of the heat exchanger.

The heat exchange fluid is circulated through the catheter body in either a reciprocal or unidirectional flow to cool or heat the patient.

In addition, the heat exchange catheter can be used with a sensor for sensing a patient's temperature and automatically changing the temperature of the heat exchange fluid in accordance with the sensing of the patient's temperature.

The heat exchange catheter can also be targeted to a local region of the digestive tract. The heat exchange fluid is circulated within the catheter body as the catheter body is directed to the targeted local region of the digestive tract. Alternatively, it can be appreciated, that the colo-rectal heat exchange device can be used simultaneously with intra vascular or other heat exchange devices to maximize the rate of heat exchange.

Figure 9:
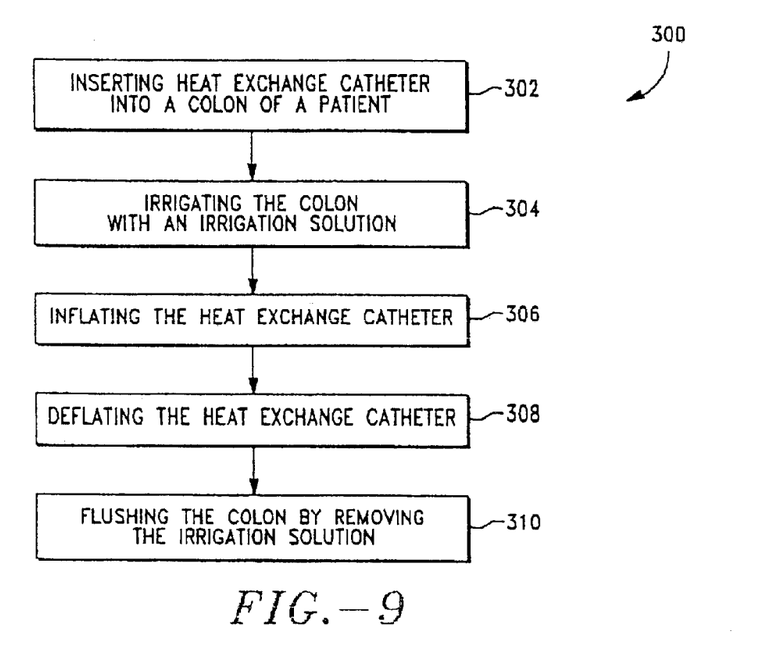
FIG. 9 is a flow diagram illustrating another method of regulating the temperature of a patient.

As shown in FIG. 9, another method of regulating patient temperature 300 includes the steps of inserting the heat exchange catheter into the lumen of the digestive tract of the patient 302. The digestive tract is then irrigated with an irrigation solution 304 and the heat exchange catheter is inflated with at least one heat exchange fluid from a temperature control unit through the inflow lumen 306. The heat exchange catheter is then deflated by removing the heat exchange fluid through the outflow lumen 308. After the heat exchange catheter is deflated, the irrigation solution is flushed from the digestive tract 310.

The heat exchange catheter body can be inserted adjacent to a targeted local region of the digestive tract to provide isolated heating and/or cooling of the targeted local region. It can be appreciated that, there may be medical conditions where, in contrast to whole body or core temperature control, a localized portion of the digestive system would benefit from a specific temperature whether it is hypothermia, maintenance of normothermia or hyperthermia. Further, depending on catheter size, configuration and use, either the temperature of a specific region of the digestive tract and/or the patient's core body temperature may be heated, cooled or regulated at a desired level.

The rate of inflation of the heat exchange catheter can be controlled by regulating a rate of flow of the heat exchange fluid. The regulation of the heat exchange fluid can be accomplished by actuating a value, or by regulating the flow by use of a pump.

The reciprocal or recirculating coolant flow may have pressure or flow characteristics that, in combination with the device design, reduce laminar coolant flow and enhance heat exchange e.g. pulsatile flow that alternately increases and decreases flow and pressure. Pulsatile flow/pressure in combination with distensible heat exchange balloons, membranes, tubes, fibers can enhance heat exchange members by moving the heat exchange members against the highly vascular wall of the intestinal lumen.

The heat exchange catheter can be used alone or in combination with other means or types of coolants for example heat pipes, electrical heaters, and RF energy.

While there has been described what are believed to be the preferred embodiment of the present invention, those skilled in the art will recognize that other and further changes and modifications may be made thereto without departing from the spirit of the invention, and it is intended to claim all such changes and modifications as fall within the true scope of the invention.

What is claimed is:

1. A method of regulating patient temperature, the method comprising:

inserting a heat exchange catheter into a colon of a patient to regulate patient temperature, the heat exchange catheter having a proximal end, a distal end, an inflow lumen, an outflow lumen and an irrigation lumen;

irrigating the colon with an irrigation solution through the irrigation lumen of the heat exchange catheter;

inflating the heat exchange catheter with at least one heat exchange fluid from a temperature control unit through the inflow lumen wherein the heat exchange fluid is circulated through the catheter body;

deflating the heat exchange catheter by removing the heat exchange fluid through the outflow lumen; and flushing the colon by removing the irrigation fluid from the colon.

2. The method according to claim 1, further comprising inflating and deflating the heat exchange catheter at least once to regulate efflux of irrigation solution.

3. The method according to claim 1, further comprising regulating pressure inside the catheter body.

4. The method according to claim 2, wherein the step of regulating includes actuating a valve to regulate pressure within the outflow lumen.

5. The method according to claim 1, wherein the step of circulating the heat exchange fluid includes circulating heat exchange fluid reciprocally.

6. The method according to claim 1, wherein the step of circulating the heat exchange fluid includes circulating heat exchange fluid unidirectionally.

7. The method according to claim 1, further comprising sensing patient temperature, and automatically changing the temperature of the heat exchange fluid in accordance with the sensed patient temperature.

8. The method according to claim 1, further comprising targeting a local region of the colon, and circulating the heat exchange fluid to the targeted region of the colon.

9. A method of regulating patient temperature, the method comprising:
   inserting a heat exchange catheter into a colon of a patient, the heat exchange catheter having a proximal end, a distal end, an inflow lumen, an outflow lumen and an irrigation lumen;
   irrigating the colon with an irrigation solution through the irrigation lumen of the heat exchange catheter;
   inflating the heat exchange catheter with at least one heat exchange fluid through the inflow lumen wherein the heat exchange fluid is circulated through the catheter body; and
   controlling the inflation of the heat exchange catheter by regulating a rate of flow of the heat exchange fluid.

10. The method according to claim 9, wherein regulating the rate of flow is accomplished by actuating a valve.

11. The method according to claim 9, wherein the rate of flow is regulated by a pump.

* * * * *